(12) United States Patent
Arzeno et al.

(10) Patent No.: US 7,745,634 B2
(45) Date of Patent: Jun. 29, 2010

(54) PROCESS FOR PREPARING TRIAZOLONES

(75) Inventors: Humberto Bartolome Arzeno, Cupertino, CA (US); Gary M. Lee, Belmont, CA (US); Michael Martin, Palo Alto, CA (US); Keshab Sarma, Sunnyvale, CA (US); Jiang Zhu, Cupertino, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 96 days.

(21) Appl. No.: 12/156,145

(22) Filed: May 30, 2008

(65) Prior Publication Data

US 2009/0012304 A1    Jan. 8, 2009

Related U.S. Application Data

(60) Provisional application No. 60/932,216, filed on May 30, 2007.

(51) Int. Cl.
*C07D 249/12*   (2006.01)
(52) U.S. Cl. .................................................. 548/264.2
(58) Field of Classification Search ............... 548/264.2
See application file for complete search history.

(56) References Cited

U.S. PATENT DOCUMENTS 7,208,509 B2    4/2007   Dunn et al.
2004/0192704 A1    9/2004   Dunn et al.
2005/0234236 A1    10/2005   Kertesz et al.
2006/0025462 A1    2/2006   Dunn et al.

*Primary Examiner*—Patricia L Morris
(74) *Attorney, Agent, or Firm*—Brian L. Buckwalter (57) ABSTRACT

The present process provides a improved method for the preparation of alkylsulfanyl substituted triazoles 2 which are useful intermediates in a new process for the preparation of triazolones 20.

8 Claims, 2 Drawing Sheets

PROCESS FOR PREPARING TRIAZOLONES

CROSS REFERENCE TO PRIOR APPLICATIONS

This application claims the benefit of priority to U.S. Ser. No. 60/932,216 filed May 30, 2007 which is hereby incorporated by reference in its entirety.

FIELD OF THE INVENTION

The present invention relates to a process for the preparation of 3-[3-(4-methyl-5-methylsulfanyl-4H-[1,2,4]triazol-3-ylmethyl)phenoxy]-5-difluoromethyl-benzonitrile derivatives according to formula 2. Compounds of formula 2 are useful for the preparation of triazolones according to formula 20 utilizing additional steps disclosed herein. Triazolones of formula 20 are useful inhibitors of HIV-1 reverse transcriptase and are useful for treating AIDS and HIV-1 mediated syndromes. The invention further provides compounds of formula 4 which are useful reagents in the presently disclosed process.

BACKGROUND OF THE INVENTION

The human immunodeficiency virus HIV is the causative agent of acquired immunodeficiency syndrome (AIDS), a disease characterized by the destruction of the immune system, particularly of the CD4+ T-cell, with attendant susceptibility to opportunistic infections. HIV infection is also associated with a precursor AIDS-related complex (ARC), a syndrome characterized by symptoms such as persistent generalized lymphadenopathy, fever and weight loss.

Currently available chemotherapy targets two crucial viral enzymes: HIV protease and HIV reverse transcriptase. (J. S. G. Montaner et al., *Biomed. & Pharmacother.* 1999 53:63-72; R. W. Shafer and D. A. Vuitton, *Biomed. & Pharmacother.* 1999 53:73-86; E. De Clercq, *Curr. Med. Chem.* 2001 8:1543-1572). Two general classes of RTI inhibitors have been identified: nucleoside reverse transcriptase inhibitors (NRTI) and non-nucleoside reverse transcriptase inhibitors. Currently the CCR5 co-receptor has emerged as a potential target for anti-HIV chemotherapy (D. Chantry, *Expert Opin. Emerg. Drugs* 2004 9(1):1-7; C. G. Barber, *Curr. Opin. Invest. Drugs* 2004 5(8):851-861; D. Schols, *Curr. Topics Med. Chem.* 2004 4(9):883-893; N. A. Meanwell and J. F. Kadow, *Curr. Opin. Drug Discov. Dev.* 2003 6(4):451-461). Drugs targeted at new enzymatic targets have entered the market including integrase inhibitors typified by Raltegravir (Merck) has been approved by the FDA and Elvitegravir (Gilead Sciences and Japan Tobacco) is in phase II trials. The CCR5 antagonist maraviroc (SELZENTRY™, Pfizer) has also been approved by the FDA for anti-HIV-1 therapy.

NNRTIs were first discovered in 1989. NNRTI are allosteric inhibitors which bind reversibly at a nonsubstrate-binding site on the HIV reverse transcriptase thereby altering the shape of the active site or blocking polymerase activity (R. W. Buckheit, Jr., *Expert Opin. Investig. Drugs* 2001 10(8)1423-1442; E. De Clercq, *Antiviral Res.* 1998 38:153-179; E. De Clercq, *Current medicinal Chem.* 2001 8(13):1543-1572; G. Moyle, *Drugs* 2001 61 (1):19-26). Initially viewed as a promising class of compounds, in vitro and in vivo studies quickly revealed the NNRTIs presented a low barrier to the emergence of drug resistant HIV strains and class-specific toxicity. Although over thirty structural classes of NNRTIs have been identified in the laboratory, only three compounds have been approved for HIV therapy: efavirenz, nevirapine and delavirdine. There remains a need for safer drugs with activity against wild type and commonly occurring resistant strains of HIV.

5-Aralkyl-2,4-dihydro-[1,2,4]triazol-3-ones are non-nucleoside reverse transcriptase inhibitors have been disclosed by J. P. Dunn et al. in U.S. Pat. No. 7,208,509 granted Apr. 24, 2007 and by J. P. Dunn et al. in U.S. Publication No. 20060025462 filed Jun. 27, 2005. Pyridazinone non-nucleoside reverse transcriptase inhibitors have been disclosed by J. P. Dunn et al. in U.S. Pat. No. 7,208,509 granted Mar. 13, 2007 and U.S. Publication No. 20050215554 published Sep. 28, 2005. A process for the preparation of pyridazinone non-nucleoside reverse transcriptase inhibitors was disclosed by D. J. Kertesz in U.S. Patent Publication 20050234236 published Oct. 20, 2005.

R = chloro, bromo, alkyl, cycloalkyl alkoxy;
Ar = phenyl substituted with cyano, halogen and/or haloalkyl

SUMMARY OF THE INVENTION

The current invention affords an improved process for the synthesis of 3-[3-(1,4-dimethyl-5-oxo-4,5-dihydro-1H-[1,2,4]triazol-3-ylmethyl)-2-fluoro-phenoxy]-5-difluoromethyl-benzonitrile derivatives which are inhibitors of HIV-1 reverse transcriptase and are useful in the treatment of HIV-1 mediated disease. The current invention provides a process for the preparation of a triazoles of formula 2 which can be transformed to the desired triazolones by process described herein. The process comprises the condensation of 6 and the conjugate base of 4 wherein Ar is phenyl substituted with 2 or 3 groups independently selected from halogen, cyano and $C_{1-6}$ haloalkyl, and $R^1$ and $R^3$ are $C_{1-10}$ alkyl, which process comprises the steps of:

(a) contacting 4 with a strong base in an inert solvent to form the conjugate base of 4 and contacting said conjugate base with 6 wherein Ar is phenyl substituted with 2 or 3 groups independently selected from halogen, cyano and $C_{1-6}$ haloalkyl to afford 8;

(b) exposing 8 to conditions which result in hydrolysis of the ester and decarboxylation of the resulting acid to afford 2.

The invention further comprises a process for replacing the nitro moiety of 2 with a chloro or bromo moiety and for further transforming the triazole 14 to a triazolone 20 which process comprises the following steps:

(c) contacting 2 with a reducing agent capable of selective reduction of the nitro group to afford 12; and, (d) contacting 12 with a diazotizing reagent and either Cu(I) Br/LiBr or Cu(I)Cl/LiCl to afford 14 wherein $R^2$ is bromo and chloro respectively.

(e) exposing 14 to an oxidizing agent capable of selective oxidation of the sulfide to a sulfone 18; and (f) contacting 18 with acetic acid/acetic anhydride under conditions which result in cleavage of the S-alkyl bond and hydrolysis of the resulting thiol to afford 20.

The present invention also provides new compounds of formula 4 wherein $R^1$ and $R^3$ are independently $C_{1-10}$ alkyl which are useful for the preparation of triazoles of formula 2 and triazolones of formula 20.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

A "stable" compound is a compound which can be prepared and isolated and whose structure and properties remain or can be made to remain essentially unchanged for a period of time sufficient to allow the use of the compound for the purposes described herein (e.g., therapeutic or prophylactic administration to a subject).

Unless expressly stated to the contrary, all ranges cited herein are inclusive. For example, a heterocyclic ring described as containing "1 to 4 heteroatoms" means the ring can contain 1, 2, 3 or 4 heteroatoms. It is also to be understood that any range cited herein includes within its scope all of the subranges within that range. Thus, for example, an aryl or a heteroaryl described as optionally substituted with "from 1 to 5 substituents" is intended to include as aspects thereof, any aryl optionally substituted with 1 to 4 substituents, 1 to 3 substituents, 1 to 2 substituents, 2 to 5 substituents, 2 to 4 substituents, 2 to 3 substituents, 3 to 5 substituents, 3 to 4 substituents, 4 to 5 substituents, 1 substituent, 2 substituents, 3 substituents, 4 substituents, and 5 substituents.

The symbols "*" at the end of a bond or "------" drawn through a bond each refer to the point of attachment of a functional group or other chemical moiety to the rest of the molecule of which it is a part. Thus, for example:

The term "inert organic solvent" or "inert solvent" as used herein means the solvent is inert under the conditions of the reaction being described in conjunction therewith, including for example, benzene, toluene, MeCN, THF, N,N-dimethylformamide, chloroform, DCM, dichloroethane, diethyl ether, EtOAc, acetone, methyl ethyl ketone, MeOH, EtOH, propanol, IPA, tert-butanol, dioxane, pyridine, and the like. Unless specified to the contrary, the solvents used in the reactions of the present invention are inert solvents. Inert solvents compatible with strong bases do not have acidic protons which are subject to abstraction and typically include aliphatic and aryl hydrocarbons, ethers such as THF, DME, diethyl ether and dioxane or polar aprotic solvents such as DMF, NMP and DMSO.

The term "strong base" as used herein refers to a basic compound of sufficient basicity to abstract a proton from the methylene carbon between the ester moiety and the triazole ring of formula 4. Typical bases which can be used include, but are not limited to, lithium dialkyl amides such as lithium diisopropylamide, lithium dicyclohexylamide, potassium or sodium tert-butoxide, lithium or sodium hexamethyldisilazane, and sodium or potassium hydride.

Selective hydrolysis of tert-butyl esters can be accomplished under acidic conditions such as TFA or HCl in ethereal solvents.

The term "diazotizing reagent" refers a reagent capable of converting an aryl amine to an aryl diazonium salt (e.g., Ph-N≡N$^+$X$^-$). Common reagents to convert an aromatic amine to a diazonium salt include nitrous acid (sodium nitrite in acid solution) or alkyl nitrite such as tert-butyl nitrite.

Oxidation of a thiol to a sulfoxide or sulfone is typically facile and numerous reagents are known which capable of carrying out this transformation. Sulfur oxidations are commonly carried out with aqueous solutions of hydrogen peroxide, $NaIO_4$, tert-butyl hypochlorite, acyl nitrites, sodium perborate, potassium hydrogen persulfate and peracids such as peracetic acid and meta-chloroperbenzoic acid. Typically with about one equivalent of oxidant the sulfone can be isolated. Exposure to two or more equivalents results in oxidation to the sulfone. Any oxidant can be utilized in the present process without departing from the spirit of the invention.

Reduction of the nitro group can be carried out with a variety of well-known reducing agents. For example an activated metal such as activated iron, zinc or tin (produced for example by washing iron powder with a dilute acid solution such as dilute hydrochloric acid). The reduction can also be carried out under a hydrogen atmosphere in the presence of an inert solvent in the presence of a metal effective to catalyze hydrogenation reactions such as platinum or palladium. Other reagents which have been used to reduce nitro compounds to amines include $AlH_3$—$AlCl_3$, hydrazine and a catalyst, $TiCl_3$, Al—$NiCl_2$-THF, formic acid and Pd/C and sulfides such as NaHS, $(NH_4)_2S$ or polysulfides (i.e. the Zinn reaction). Aromatic nitro groups have been reduced with $NaBH_4$ or $BH_3$ in the presence of catalysts such as $NiCl_2$ and $CoCl_2$. Thus for example, reduction may be effected by heating the nitro group in the presence of a sufficiently activated metal such as Fe and a solvent or diluent such as $H_2O$ and alcohol, for example MeOH or EtOH at a temperature in the range of 50 to 150° C., conveniently at about 70° C. (J. March, *Advanced Organic Chemistry*, John Wiley & Sons: New York, N.Y., 1992, p. 1216). All reducing conditions capable of selective reduction of the nitro group in intermediates described herein are with the scope of the invention.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

The term "halogen" or "halo" as used herein means fluorine, chlorine, bromine, or iodine.

The term "haloalkyl" as used herein denotes a unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

In one embodiment of the present invention there is provided a process for the preparation of a compound according to formula 2 which process comprises the steps of (a) contacting 4 with a strong base in an inert solvent said strong base capable of forming the conjugate base of 4 and contacting said conjugate base with 6 to afford 8; and, (b) exposing 8 to reaction conditions which capable of hydrolyzing the ester and decarboxylating the resulting carboxylic acid 8a wherein Ar is phenyl substituted with 2 or 3 groups independently selected from halogen, cyano and $C_{1-6}$ haloalkyl, and $R^1$ and $R^3$ are $C_{1-10}$ alkyl.

a second embodiment of the present invention there is provided a process for the preparation of a compound according to formula 2 which process comprises the steps of (a) contacting 4 with a strong base in an inert solvent said strong base capable of forming the conjugate base of 4 and contacting said conjugate base with 6 to afford 8; and, (b) exposing 8 to reaction conditions which capable of hydrolyzing the ester and decarboxylating the resulting carboxylic acid 8a wherein Ar is 3-chloro-5-cyano-phenyl, 3,5-dicyano-phenyl or 3-cyano-5-difluoromethyl-phenyl, $R^1$ is methyl and $R^3$ is tert-Bu.

In a third embodiment of the present invention there is provided a process for the preparation of a compound according to formula 2 which process comprises the steps of (a) contacting 4 with a strong base in an inert solvent said strong base capable of forming the conjugate base of 4 and contacting said conjugate base with 6 to afford 8; and, (b) exposing 8 to reaction conditions which capable of hydrolyzing the ester and decarboxylating the resulting carboxylic acid 8a wherein Ar is 3-chloro-5-cyano-phenyl, 3,5-dicyano-phenyl or 3-cyano-5-difluoromethyl-phenyl, $R^1$ is methyl and $R^3$ is tert-Bu, said strong base is potassium tert-butoxide, said inert solvent is THF and said hydrolysis conditions comprise methanesulfonic acid in acetonitrile at reflux temperature.

In a fourth embodiment of the present invention there is provided a process for the preparation of a compound according to formula 2 which process comprises the steps of (a) contacting 4 with a strong base in an inert solvent said strong base capable of forming the conjugate base of 4 and contacting said conjugate base with 6 to afford 8; and, (b) exposing 8 to reaction conditions which capable of hydrolyzing the ester and decarboxylating the resulting carboxylic acid 8a wherein Ar is 3-cyano-5-difluoromethyl-phenyl, $R^1$ is methyl and $R^3$ is tert-Bu, said strong base is potassium tert-butoxide, said inert solvent is THF and said hydrolysis conditions comprise methanesulfonic acid in acetonitrile at reflux temperature.

In a fifth embodiment of the present invention there is provided a process for the preparation of a compound according to formula 2 which process comprises the steps of (a) contacting 4 with a strong base in an inert solvent said strong base capable of forming the conjugate base of 4 and contacting said conjugate base with 6 to afford 8; (b) exposing 8 to reaction conditions which capable of hydrolyzing the ester and decarboxylating the resulting carboxylic acid 8a; (c) contacting 2 with a reducing agent capable of selective reduction of the nitro group to afford 12; and, (d) contacting 12 with a diazotizing reagent and either Cu(I)Br/LiBr or Cu(I)Cl/LiCl to afford 14 wherein $R^2$ is bromo and chloro respectively, Ar is phenyl substituted with 2 or 3 groups independently selected from halogen, cyano and $C_{1-6}$ haloalkyl and $R^1$ and $R^3$ are $C_{1-10}$ alkyl. One skilled in the art will appreciate that other chloride and bromide salts can be used in place of the lithium salts recited herein without departing from the spirit of the invention.

In a sixth embodiment of the present invention there is provided a process for the preparation of a compound according to formula 2 which process comprises the steps of (a) contacting 4 with a strong base in an inert solvent said strong base capable of forming the conjugate base of 4 and contacting said conjugate base with 6 to afford 8; (b) exposing 8 to reaction conditions which capable of hydrolyzing the ester and decarboxylating the resulting carboxylic acid 8a, (c) contacting 2 with a reducing agent capable of selective reduction of the nitro group to afford 12; and, (d) contacting 12 with a diazotizing reagent and Cu(I)Br/LiBr to afford 14 wherein $R^2$ is bromo, Ar is 3-cyano-5-difluoromethyl-phenyl, $R^1$ is methyl, $R^3$ is tert-butyl, said strong base is potassium tert-butoxide, said inert solvent is THF, said hydrolysis conditions comprise methanesulfonic acid in acetonitrile at reflux temperature, said reducing agent is hydrogen, Pd/C and VO(acac)$_2$ and said diazotizing reagent is tert-butyl nitrite.

In a seventh embodiment of the present invention there is provided a process for the preparation of a compound according to formula 2 which process comprises the steps of (a) contacting 4 with a strong base in an inert solvent said strong base capable of forming the conjugate base of 4 and contacting said conjugate base with 6 to afford 8; (b) exposing 8 to reaction conditions which capable of hydrolyzing the ester and decarboxylating the resulting carboxylic acid 8a, (c) contacting 2 with a reducing agent capable of selective reduction of the nitro group to afford 12; (d) contacting 12 with a diazotizing reagent and Cu(I)Br/LiBr to afford 14 wherein $R^2$ is bromo, Ar is 3-cyano-5-difluoromethyl-phenyl, $R^1$ is methyl, $R^3$ is tert-butyl, said strong base is potassium tert-butoxide, said inert solvent is THF, said hydrolysis conditions comprise methanesulfonic acid in acetonitrile at reflux temperature, said reducing agent is hydrogen, Pd/C and VO(acac)$_2$, said diazotizing reagent is tert-butyl nitrite; and (e) converting 14 to the tosylate salt and recrystallizing said salt.

In an eighth embodiment of the present invention there is provided a process for the preparation of a compound according to formula 2 which process comprises the steps of (a) contacting 4 with a strong base in an inert solvent said strong base capable of forming the conjugate base of 4 and contacting said conjugate base with 6 to afford 8; (b) exposing 8 to reaction conditions which capable of hydrolyzing the ester and decarboxylating the resulting carboxylic acid 8a; (c) contacting 2 with a reducing agent capable of selective reduction of the nitro group to afford 12; (d) contacting 12 with a diazotizing reagent and Cu(I)Br/LiBr to afford 14; (e) exposing 14 to an oxidizing agent capable of oxidation of the sulfide to a sulfone 18; and (f) contacting 18 with acetic acid/acetic anhydride under conditions which result in cleavage of the S-heteroaryl bond and hydrolysis of the resulting acetate to afford 20 wherein $R^2$ is bromo, Ar is 3-cyano-5-difluoromethyl-phenyl, and $R^1$ is methyl and $R^3$ are tert-butyl.

In a ninth embodiment of the present invention there is provided a process for the preparation of a compound according to formula 2 which process comprises the steps of (a) contacting 4 with a strong base in an inert solvent said strong base capable of forming the conjugate base of 4 and contacting said conjugate base with 6 to afford 8, (b) exposing 8 to reaction conditions which capable of hydrolyzing the ester and decarboxylating the resulting carboxylic acid 8a, (c) contacting 2 with a reducing agent capable of selective reduction of the nitro group to afford 12; (d) contacting 12 with a diazotizing reagent and either Cu(I)Br/LiBr to afford 14, (e) exposing 14 to an oxidizing agent capable of oxidation of the sulfide to a sulfone 18; and (f) contacting 18 with acetic acid/acetic anhydride under conditions which result in cleavage of the S-heteroaryl bond and hydrolysis of the resulting acetate to afford 20 wherein $R^2$ is bromo; wherein Ar is 3-cyano-5-difluoromethyl-phenyl, $R^1$ is methyl, $R^3$ is tert-butyl, said strong base is potassium tert-butoxide, said inert solvent is THF, said hydrolysis conditions comprise methane sulfonic acid in acetonitrile at reflux temperature said reducing agent is hydrogen, Pd/C and VO(acac)$_2$, said diazotizing reagent is tert-butyl nitrite, and said oxidizing agent is MCBPA.

In a tenth embodiment of the present invention there is provided a compound according to formula 4 wherein $R^1$ and $R^3$ are independently $C_{1-10}$ alkyl.

In an eleventh embodiment of the present invention there is provided a compound according to formula 4 wherein $R^1$ is methyl and $R^3$ is tert-butyl.

In a twelfth embodiment of the present invention there is provided a process for preparing a compound according to formula 4 said process comprising the steps of (a) contacting a half ester of malonic acid with CDI in an inert solvent to form a 3-imidazol-1-yl-3-oxo-propionic acid ester (21), (b) contacting the resulting acylimidazole from step (a) with the thiosemicarbazide 22; and (c) treating the resulting 5-thioxo-4,5-dihydro-1H-[1,2,4]triazole-3-carboxylate 24 with an alkylating agent to afford 4 wherein $R^1$ and $R^3$ are $C_{1-10}$.

In a thirteenth embodiment of the present invention there is provided a process for preparing a compound according to formula 4 said process comprising the steps of (a) contacting a half ester of malonic acid with CDI in an inert solvent to form a 3-imidazol-1-yl-3-oxo-propionic acid ester (21), (b) contacting the resulting acylimidazole from step (a) with the thiosemicarbazide 22; and (c) treating the resulting 5-thioxo-4,5-dihydro-1H-[1,2,4]triazole-3-carboxylate 24 with an alkylating agent to afford 4 wherein $R^1$ is Me and $R^3$ is tert-Bu, said half ester of malonic acid is tert-butyl hydrogen malonate and said alkylating agent is methyl iodide.

In a fourteenth embodiment of the present invention there is provided a process for the preparation of a compound according to formula 2 which process comprises the steps of: (a) contacting 3,5-dibromo-fluoro-benzene (25) with iso-propyl magnesium chloride to afford a 3-bromo-5-fluoro-phenylmagnesium halide (26); (b) contacting 26 with DMF followed by aqueous acid and MTBE to afford 3-bromo-5-fluoro-benzaldehyde (28); (c) contacting 28 with DEOXO-FLUOR and DCM to a afford 3-fluoro-5-difluoromethyl-1-bromo-benzene (30); (d) contacting 30 with p-methoxy-benzyl alcohol and potassium tert-butoxide in THF to afford 1-bromo-3-difluoromethyl-5-(4-methoxy-benzyloxy)-benzene (32); (e) contacting a solution of 32 and NMP with potassium ferrocyanide, $Na_2CO_3$, $Pd(OAc)_2$ and DPPF at about 130° C. to afford 34; (f) treating a solution of 34 and anisole with TFA at temperatures sufficient to cleave the O-benzyl linkage and afford 36; (g) treating a solution of 36 and THF with 1,2,3-trifluoro-4-nitrobenzene (37) and $K_2CO_3$ to afford 3-difluoromethyl-5-(2,3-difluoro-6-nitro-phenoxy)-benzonitrile (38); (h) contacting 4 with a strong base in an inert solvent said strong base capable of forming the conjugate base of 4 and contacting said conjugate base with 6 to afford 8; (i) exposing 8 to reaction conditions which are capable of hydrolyzing the ester and decarboxylating the resulting carboxylic acid 8a, (j) contacting 2 with a reducing agent capable of selective reduction of the nitro group to afford 12; (k) contacting 12 with a diazotizing reagent and either Cu(I)Br/LiBr or Cu(I)Cl/LiCl to afford 14, (l) exposing 14 to an oxidizing agent capable of oxidation of the sulfide to a sulfone 18; and (m) contacting 18 with acetic acid/acetic anhydride under conditions which result in cleavage of the S-heteroaryl bond and hydrolysis of the resulting acetate to afford 20 wherein $R^2$ is bromo and chloro respectively, Ar is phenyl substituted with 2 or 3 groups independently selected from halogen, cyano and $C_{1-6}$ haloalkyl, and $R^1$ and $R^3$ are $C_{1-10}$ alkyl.

In a fifteenth embodiment of the present invention there is provided a process for the preparation of a compound according to formula 2 which process comprises the steps of: (a) contacting 25 with p-methoxy-benzyl alcohol and potassium tert-butoxide in THF to afford 40; (b) contacting 40 with iso-propyl magnesium chloride to afford 41; (b) contacting 41 with DMF followed by aqueous acid and MTBE to afford 42; (d) contacting a solution of 42 and NMP with potassium ferrocyanide $Na_2CO_3$, $Pd(OAc)_2$ and DPPF at 130° C. to afford 44; (e) treating a solution of 44 and anisole with TFA at temperatures sufficient to cleave the O-benzyl linkage and afford 46; (g) treating a solution of 46 and THF with 1,2,3-trifluoro-4-nitrobenzene (37) and potassium carbonate to afford 48; (h) contacting 48 with DEOXO-FLUOR and DCM to a afford 38; (g) contacting 4 with a strong base in an inert solvent said strong base capable of forming the conjugate base of 4 and contacting said conjugate base with 6 to afford 8; (h) exposing 8 to reaction conditions which capable of hydrolyzing the ester and decarboxylating the resulting carboxylic acid 8a, (i) contacting 2 with a reducing agent capable of selective reduction of the nitro group to afford 12; (j) contacting 12 with a diazotizing reagent and either Cu(I)Br/LiBr or Cu(I)Cl/LiCl to afford 14, (k) exposing 14 to an oxidizing agent capable of oxidation of the sulfide to a sulfone 18; and (l) contacting 18 with acetic acid/acetic anhydride under conditions which result in cleavage of the S-heteroaryl bond and hydrolysis of the resulting acetate to afford 20 wherein $R^2$ is bromo and chloro respectively, Ar is phenyl substituted with 2 or 3 groups independently selected from halogen, cyano and $C_{1-6}$ haloalkyl, and $R^1$ and $R^3$ are $C_{10}$ alkyl.

Commonly used abbreviations include: acetyl (Ac), atmospheres (Atm), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), diethylaminosulfur trifluoride (DAST), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), bis-(2-methoxyethyl)amine sulfur trifluoride (DEOXO-FLUOR), di-iso-propylazodicarboxylate (DLAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ferrocene (DPPF), 1-(3-dimethylaminopropyl)-3-ethylcarbodiimide hydrochloride (EDCI), ethyl (Et), ethyl acetate (EtOAc), ethanol (EtOH), diethyl ether ($Et_2O$), acetic acid (HOAc), high pressure liquid chromatography (HPLC), iso-propanol (IPA), lithium hexamethyl disilazane (LiHMDS), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), N-bromosuccinimide (NBS), N-chlorosuccinimide (NCS), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), tert-butyldimethylsilyl or t-$BuMe_2Si$ (TBDMS), triethylamine (TEA or $Et_3N$), 2,2,6,6-tetramethylpiperidine 1-oxyl (TEMPO), triflate or $CF_3SO_2$— (Tf), trifluoroacetic acid (TFA), 1,1'-bis-2,2,6,6-tetramethylheptane-2,6-dione (TMHD), thin layer chromatography (TLC), tetrahydrofuran (THF), trimethylsilyl or $Me_3Si$ (TMS), p-toluenesulfonic acid monohydrate (TsOH or pTsOH), 4-Me—$C_6H_4OS_2$— or tosyl (Ts), Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford).

Process

5-Aralkyl-triazolones A-2 have been prepared by condensation of an acyl hydrazide A-1b with methyl isocyanate to yield an N-acyl-N-carbamoylhydrazide A-1c which was cyclized to A-2 by treatment with methanolic potassium hydroxide.

SCHEME A

While this sequence provided access to triazolone NNRTIs, experience so showed that the reaction could be capricious and was not suitable for larger scale synthesis. A new route which has proven general, convenient and amenable to large scale synthesis now has been identified.

The process provided herein comprises $S_NAr$ displacement of an aromatic fluoride with the enolate derived from an alkyl (4-alkyl-5-alkylsulfanyl-4H-[1,2,4]triazol-3-yl)-acetate. The resulting aralkyl ester is hydrolyzed and decarboxylated and the alkylthio triazole converted to the desired triazolone under mild reaction conditions.

In U.S. Patent Publication 2005/0234236, published Oct. 20, 2005, D. J. Kertesz et al. disclose the arylation of alkyl (5-alkyl-6-oxo-1,6-dihydro-pyridazin-3-yl)-acetates and dialkyl malonates with 2-aryloxy-3,4-difluoro-nitrobenzenes to afford 6-benzyl-4-methyl-2H-pyridazin-3-one derivatives and 3-aryloxy-phenyl acetic acid derivatives. The requisite 2-aryloxy-3,4-difluoro-nitrobenzenes have been prepared by treating 2,3,4-trifluoro-nitrobenzene with an appropriately substituted phenol resulting in the displacement of the 2-fluoro substituents with good regioselectivity. An analogous sequence leading to 3-aryloxy-phenylacetic acids has been described by J. P. Dunn et al. in U.S. Pat. No. 7,166,730 published Jan. 23, 2007.

Figure 2:
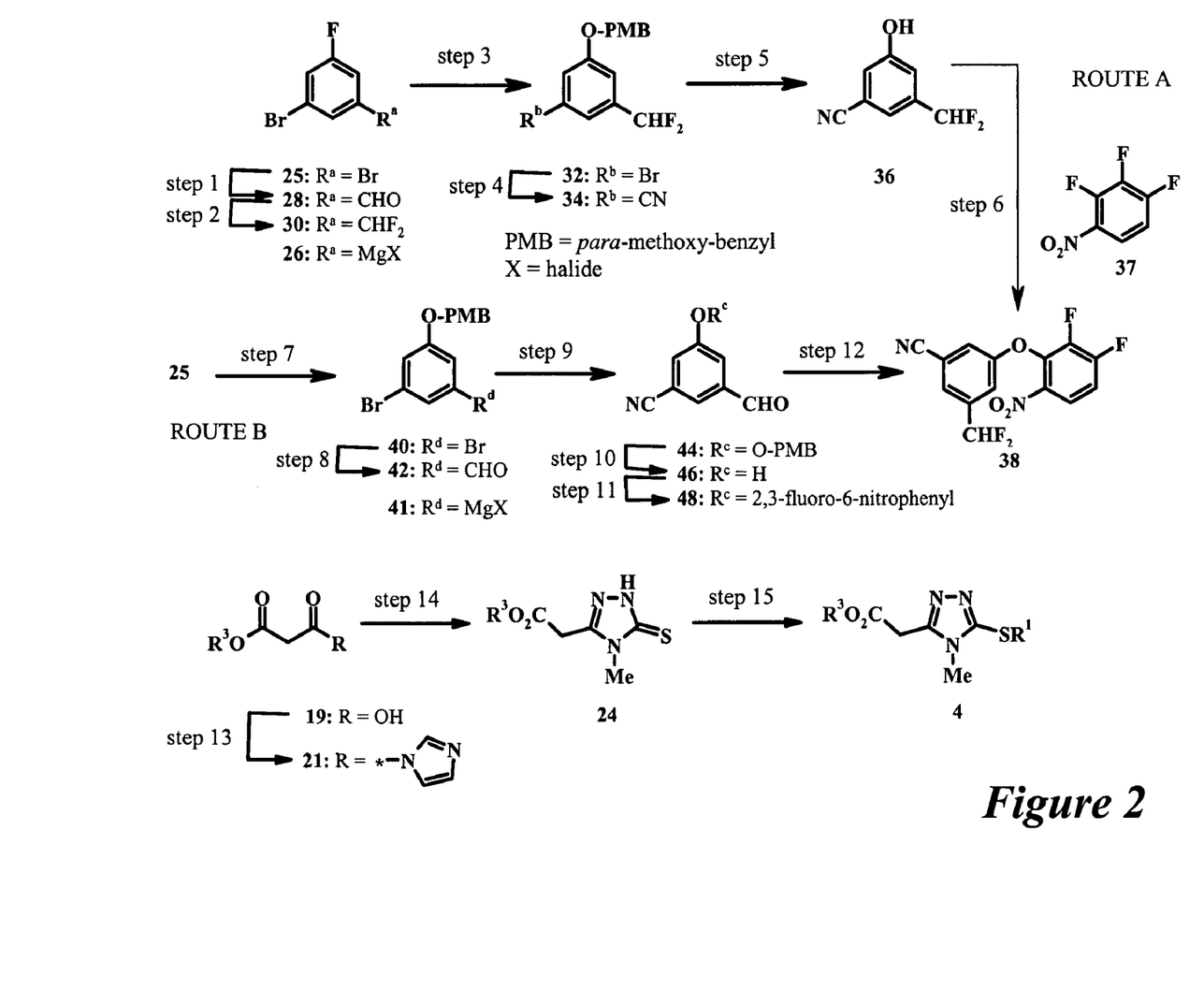
FIG. 2 depicts the process for the preparation of 3-difluoromethyl-5-(2,3-difluoro-6-nitro-phenoxy)-benzonitrile (38) and (4-methyl-5-methylsulfanyl-4H-[1,2,4]triazol-3-yl)-acetic acid tert-butyl ester 4 ($R^1$ and $R^3$=methyl)

Two routes for the preparation of 3-difluoromethyl-5-(2,3-difluoro-6-nitro-phenoxy)-benzonitrile are depicted in FIG. 2. Both routes commence with 3,5-dibromo-fluoro-benzene (25) utilizing similar reactions but the sequence of the reactions differ. Route A begins by selective monometallation of 25 and formylation of the resulting aryl Grignard reagent. Fluorination of aldehyde results in the introduction of the requisite difluoromethyl substituent 30.

Aldehydes and ketones are converted an be converted into difluoro compounds with fluorinating reagents such as SF4/Lewis Acids, DAST (diethylaminosulfur trifluoride), bis-(2-methoxyethyl)aminosulfur trifluoride in non-polar and non-basic solvent.

Aryl fluorides are generally significantly more labile than other halogen substituents. While hard nucleophiles like water and hydroxide fail to displace fluoride, soft nucleophiles like phenols, imidazoles, amines, thiols and some amides facilely displace fluorine at room temperature (D. Boger et al., *Biorg. Med. Chem. Lett.* 2000 10: 1471-75; F. Terrier *Nucleophilic Aromatic Displacement: The Influence of the Nitro Group* VCH Publishers, New York, N.Y. 1991).

Displacement of the fluoride with potassium salt of p-methoxy-benzyl alcohol affords a protected phenol.

Palladium-mediated displacement of the bromo substituent with potassium ferrocyanide and Pd(OAc)$_2$ in the presence of DPPF afforded the requisite benzonitrile 34 which could be deprotected by exposure to acid resulting in the expulsion of a p-methoxy-benzyl carbonium ion which is trapped with anisole to afford 36.

The reaction of sodium methoxide with 2,3,4-trifluoronitrobenzene in methanol has been reported to afford an inseparable mixture of the corresponding 2- and 4-monomethoxy and 2,4-dimethoxy derivatives (P. M. O'Neill et al., *J. Med. Chem.* 1994 37:1362-70). Displacement of the ortho-fluorine of 2,4-difluoronitrobenzene by amine nucleophiles also has been reported. (W. C. Lumma, Jr. et al., *J. Med. Chem.* 1981 24:93-101).

The reaction of 2,3,4-trifluoronitrobenzene (Aldrich catalog No. 33, 836-2) with 3-difluoromethyl-5-hydroxy-benzonitrile resulted in regiospecific displacement of the 2-fluoro moiety to afford 38. One skilled in the art will immediately appreciate that although the process is exemplified with 36, a large number of substituted phenols or hydroxyl substituted heteroaromatic compounds are readily available and could be used to afford many other anti-HIV-compounds.

The displacement reaction can be run in a variety of organic solvents including, but not limited to, ethers (e.g. diethyl ether, THF, DME and dioxane) and alcohols (e.g., iso-propanol and sec-butanol). Solvents capable of reacting with the fluoronitrobenzene are clearly precluded as are solvents which may result in the loss of regiochemical control. Thus secondary and tertiary alcohols are acceptable solvents but primary alcohols can displace fluoride. The skilled chemist would be capable of identifying acceptable solvents with minimal experimentation. The phenol is treated with base to afford the phenolate salt. Any alkali metal salt can be employed in the present process but the reaction is conveniently carried out with the lithium, sodium or potassium salts. Sodium phenolates are readily available by treating the phenol with sodium tert-butoxide or sodium tert-amylate in tert-butanol or tert-amyl alcohol respectively. The sodium alcoholate can be prepared by treating the alcohol with sodium metal or sodium hydride. Potassium phenolates can be prepared analogously. Alternatively the phenol can be combined with the sodium alcoholate in THF to afford the salt. The reaction can be run from about −30° C. to about 40° C. without significant degradation of the regioselectivity. Typically the reactants are combined at low temperature and allowed to warm to RT after an initial mixing. Under these conditions the aromatic nucleophilic displacement proceeds with high regioselectivity at the 2-position of the substrate.

The alternate route (FIG. 2, ROUTE B) proceeds by initially introducing the PMB moiety which is sequentially formylated and treated with potassium ferrocyanide and Pd(OAc)$_2$ in the presence of DPPF to afford 44. Acid-catalyzed debenzylation and condensation with 2,3,4-trifluoronitrobenzene affords 48. Finally fluorination of the formyl moiety with DEOXOFLUOR provides 36.

tert-Butyl (4-methyl-5-methylsulfanyl-4H-[1,2,4]triazol-3-yl)acetate (4, $R^1$=methyl, $R^3$=tert-butyl) was prepared by contacting tert-butyl hydrogen malonate with carbonyl diimidazole to form the acylimidazole which is acylated with 4-methyl-3-thiosemicarbazide which subsequently undergoes intramolecular cyclization to afford 24 (FIG. 2). S-Alkylation proceeds rapidly when 24 is exposed to an alkylating agent. While methyl iodide is used in the example one skilled in the art will recognize that other thioalkyl groups will function in a similar manner and exemplification of the reaction scheme with a thiomethyl group should not presumed to be limiting. Similarly the reaction is exemplified with a tert-butyl ester, which is conveniently removed by acid treatment under mild conditions. Other esters, which may be more efficiently hydrolyzed under basic conditions, can be used without difficulty.

Contacting tert-butyl (4-methyl-5-methylsulfanyl-4H-[1,2,4]triazol-3-yl)-acetate with potassium tert-butoxide and 36 resulted in the displacement of the 4-fluoro substituent afforded 8 which was hydrolyzed with methane sulfonic acid. (FIG. 1) When the reaction was carried out at elevated temperatures the acid underwent concomitant decarboxylation to afford 2. Catalytic hydrogenation of the nitro group was carried out in the presence of Pd on carbon and vanadium acetylacetonate which cleanly afford the corresponding amine which could be converted the corresponding bromo or chloro substituent by diazotizing the amine with tert-butyl nitrite in the presence of cuprous bromide and LiBr (or CuCl/LiCl to afford the corresponding chloride) which produced 14 ($R^1$=Me, $R^2$=Br and Ar=3-cyano-5-difluoromethyl-phenyl).

Figure 1:
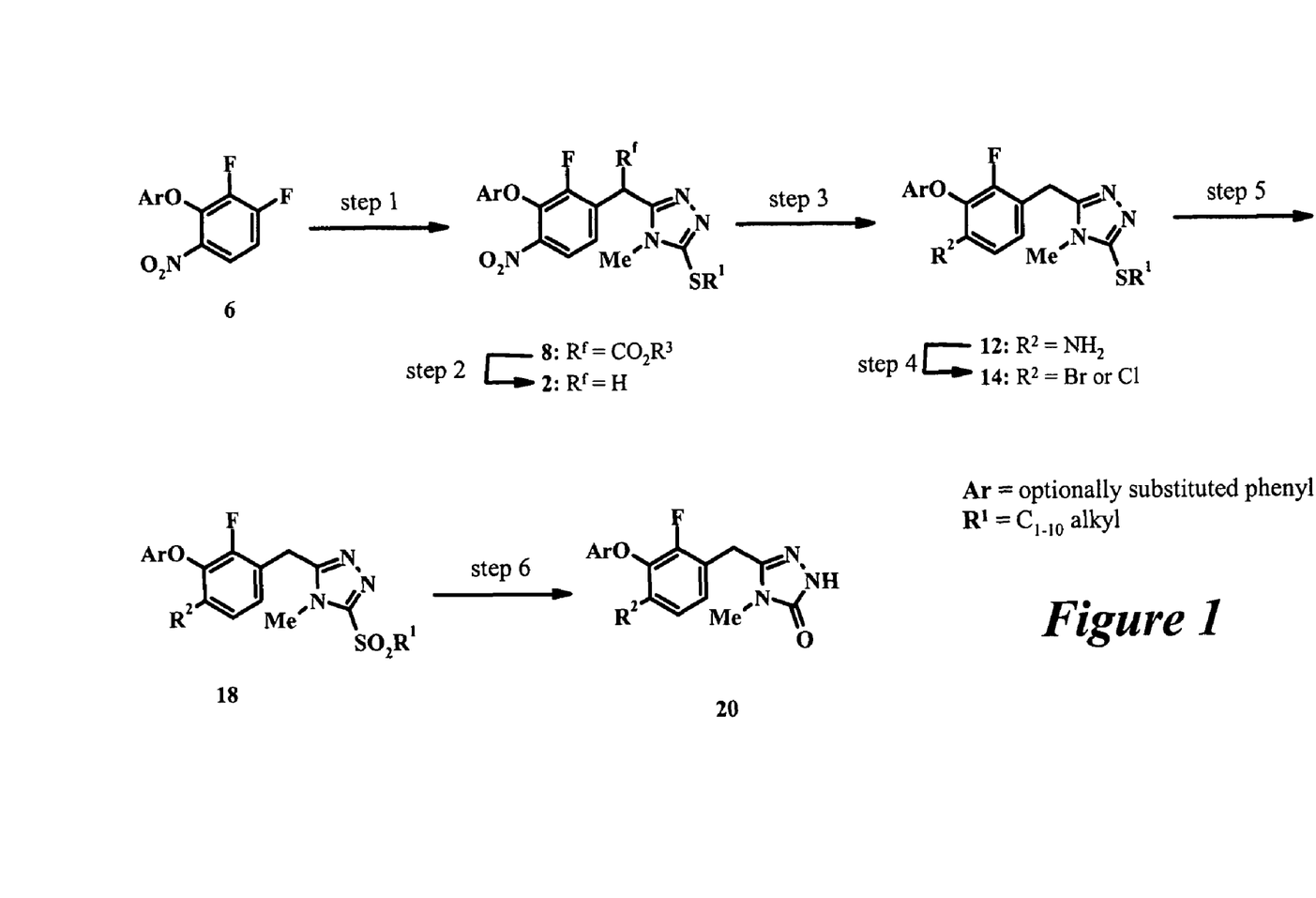
FIG. 1 depicts the process for the preparation of 3-aryloxy-2-fluoro-1-(4-methyl-5-methylsulfanyl-4H-[1,2,4]triazol-3-ylmethyl)phenyl derivatives 2 and 5-(4-halo-2-fluoro-3-aryloxy-benzyl)-4-methyl-2,4-dihydro-[1,2,4]triazol-3-one derivatives 20.

Finally elaboration of the triazolone ring was completed by oxidation of the thiomethyl to the sulfoxide. S-oxidation reactions can be performed using a 30% aqueous solution of hydrogen peroxide, or by other oxidizing agents such as, $NaIO_4$, tert-butyloxychloride, acyl nitrites, sodium perborate and peracids. Sulfides can be oxidized to sulfoxides which can be further oxidized to sulfones by addition of another equivalent of hydrogen peroxide, $KMnO_4$, sodium perborate, potassium hydrogen persulfate, peracids or the like reagents. If enough oxidizing agent is present, sulfides can be converted directly to sulfones without isolation of the sulfoxides. Exposure of the sulfone to acetic anhydride and acetic acid resulted in replacement of the methyl sulfone with an acetate and hydrolysis of the intermediate acetate to afford 20.

EXAMPLE 1

3-Difluoromethyl-5-(2,3-difluoro-6-nitrophenoxy) benzonitrile (FIG. 2; ROUTE A)

step 1—To a solution of iso-propylmagnesium chloride in THF (500 mL of a 2M solution in THF, 1.0 mol) and THF (200 mL) was added a solution of 3,5-dibromofluorobenzene (25; 200 g, 0.79 mol) in THF (100 mL) while maintaining the temperature at ca. 0 C. After rinsing with THF (3×20 mL) the mixture was aged for 2 h at ca. 0° C. and then warmed to ca. 20° C. and aged for 0.5 h. The reaction was sampled by HPLC and then cooled to ca. 0° C. DMF was added over 0.5 h while maintaining the temperature at ca. 0° C. The mixture was aged 1.5 h at ca. 0° C. and then warmed slowly to ca. 20° C. overnight. After sampling by HPLC, the mixture was diluted with heptane (200 mL) and then with a mixture of con HCl (120 mL) diluted to 360 mL with water. Con HCl (50 mL) was added to adjust the pH to <7. The organic phase was separated, washed with water (400 mL) and evaporated to dryness to afford 160.8 g (100.5%) of 28 as a yellow oil which solidified on standing.

step 2—To a solution of 28 (144.1 g, 0.71 mol) in THF cooled to a. 0° C. was added and DEOXO-FLUOR® (bis-(2-methoxyethyl)amine sulfur trifluoride; 218 mL, 261.6 g, 1.18 mol) in one portion. The mixture was warmed to RT, aged for 3 h and the reaction monitored by HPLC. The excess reagent was quenched by transferring the reaction into saturated $NaHCO_3$ (1200 mL). The organic phase was separated, washed with 1.5 N HCl (1000 mL), a mixture of water (250 mL) and saturated $NaHCO_3$ (250 mL), and finally with water (500 mL). The organic phase was concentrated to afford an oil which was fractionally distilled under vacuum to afford 98.1 g (61.3%) of 30.

steps 3-5—p-Methoxybenzyl alcohol (36.8 g, 266.7 mmol) was added slowly to a mixture of potassium t-butoxide (28.7 g, 255.5 mol) and THF (250 mL). After stirring for about 15 min, 30 (50.0 g, 222.2 mmol) was added and the reaction mixture heated to about 65° C. After stirring at 65° C. for 2 h, the reaction is analyzed by HPLC. After cooling to RT, a mixture of saturated $NaHCO_3$ solution (150 mL) and water (150 mL) was added. Toluene (300 mL) was added, the organic phase separated and washed with a mixture of saturated $NaHCO_3$ solution (75 mL) and water (75 mL). Polish filtration and concentration in vacuo provided 83.9 g of crude 32 as an oil which is used without further purification.

To a solution of crude 32 in NMP (180 ml) was added potassium ferrocyanide (31.1 g, 84.44 mmol) and $Na_2CO_3$ (23.55 g, 222.2 mmol). The resulting slurry was degassed thoroughly via repeated evacuation and purging with nitrogen. The slurry was heated to about 100° C. and a solution of $Pd(OAc)_2$ (150 mg, 0.67 mmol) and DPPF (505 mg, 0.91 mmol) in degassed NMP (20 mL) added. The mixture was heated to ca. 130° C. for about 3 h. HPLC analysis indicated ca. 5% starting material remained. Additional $Pd(OAc)_2$ (50 mg, 0.22 mmol) is added and heating at 130° C. was continued for 1.5 h when HPLC analysis showed complete conversion.

After cooling toluene (400 mL) and saturated sodium sulfite solution (10 mL) are added and mixture heated at ca. 40° C. for about 1 h. Solka-floc (10 g) was added and the mixture was filtered through a bed of Solka-floc and the cake was washed with toluene (ca. 100 mL total). The filtrate was washed successively with dilute sodium sulfite solution (1×400 mL) and water (2×200 mL). The combined aqueous phases are extracted with toluene (1×100 mL) and the toluene back extracted with water (2×50 mL). The combined organic phases are polish filtered, and concentrated in vacuo to obtain 70.4 g of 34 as a dark-colored oil (70.4 g) which was used in the next step without further purification.

To the solution of crude 36 in toluene (190 mL) and anisole (65 mL) is added TFA (25.3 g, 222.2 mmol). The reaction was heated to ca. 65° C. and stirred for about 2 h until the reaction was complete by HPLC. The mixture was distilled in vacuo to remove most of the TFA. After cooling, the mixture is extracted twice with ca. 10% $Na_2CO_3$ solution (300 mL then 150 mL). The combined aqueous phases were acidified to a pH of 5.5 with con HCl and extracted with EtOAc (2×200 mL). The combined organic phases were washed with water (1×150 ml), polish filtered and the solvent replaced with toluene by vacuum distillation. The solution was concentrated to ca. 200 mL, then heptane (200 mL) was slowly added and the mixture heated to 80° C. The mixture was cooled to RT, aged overnight, filtered, and washed with 50% heptane in toluene (ca. 30 mL). The isolated product was dried in vacuo at ca. 60° C. to afford 29.0 g (77.2% yield over 3 steps) of 36.

step 6—To a solution of 36 (0.80 g, 4.73 mmol) in THF (4.0 mL) was added slowly via syringe pump (ca. 4.5 h) a mixture of 37 (0.57 mL, 0.88 g, 4.97 mmol) and $K_2CO_3$ (1.96 g, 14.2 mmol) in THF (2.4 mL) at 0° C. The reaction was aged at 0° C. until complete. Acetic acid (0.82 mL, 0.85 g, 14.2 mmol) was added while maintaining the temperature at 5° C., followed by water (4.0 mL), and the mixture as warmed to RT. After phase separation, the organic layer was washed with saturated NaCl (5 mL), concentrated, and the product purified by $SiO_2$ chromatography eluting with 20% EtOAc/hexane to afford 1.24 g (80%) of 38 as an oil which crystallized on standing. An analytical sample obtained by recrystallization from IPA/hexane.

EXAMPLE 2

3-Difluoromethyl-5-(2,3-difluoro-6-nitrophenoxy) benzonitrile (FIG. 2; ROUTE B)

step 7—p-Methoxybenzyl alcohol (12.4 kg, 89.8 mol) was added slowly to a mixture of potassium tert-butoxide (10.0 kg, 89.4 mol) in THF (78 L) allowing the reaction exotherm to raise the temperature to ca. 35° C. After stirring at 35 to 40° C. for 0.5 h, 25 (21.4 kg, 84.3 mol) was added slowly allowing the reaction to exotherm to reach ca. 60° C. After stirring at 60° C. for 2 h the reaction was monitored by hplc. After cooling to RT, HOAc (ca. 600 g) and then water (30 L) was added and the phases separated. The aqueous phase was extracted with EtOAc (20 L) and the combined organic phases washed with a mixture of saturated brine (10 kg) and water (10 L). The organic phase was concentrated in vacuo (ca. 27 inches Hg, jacket temperature ca. 65° C.) to afford an oil. MeOH (ca. 43 kg) was added to form a biphasic mixture which was aged at 45 to 50° C. The product precipitated and the slurry was stirred until a uniform consistency was achieved. After cooling to RT, and aging overnight, the product was filtered off, washed with MeOH (9.8 kg), and dried under vacuum at 50° C. to afford 26.06 kg of 40. The material remaining in the reactor and filter was dissolved in THF (ca. 10 L) and the solution evaporated to dryness on a rotary evaporator to afford an additional 3.44 kg (94% overall)

step 8—To a solution of 40 (387 g, 1.04 mol) in THF (1.2 L) at RT was added iso-propyl magnesium chloride (0.7 L of a 2M solution in THF, 1.4 mol) over ca. 15 min while maintaining the temperature between 20 and 25° C. (mild exotherm). After aging 3 to 4 h the reaction was sampled to ascertain whether the reaction was complete (HPLC). The mixture was cooled in a salt/ice bath (<−5° C.) and DMF (250 mL, 3.2 mol) added for several min (the addition is exothermic and should be controlled to maintain the temperature at <30° C.). After aging 30 min, the mixture was quenched by adding to a mixture of tert-butyl methyl ether (1 L) and 1M $H_2SO_4$ (2 L). The organic phase was separated and washed with saturated $NaHCO_3$ (1 L), water (1 L), dried ($MgSO_4$), filtered and evaporated to dryness. The product was dissolved in EtOAc (0.4 L) and heptane (0.8 L) and $SiO_2$ (340 g, 230-400 mesh) was added and stirred for 2 h. The $SiO_2$ is filtered off, washed with a 33% EtOAc in heptane (0.6 L) and evaporated to dryness to afford 345 g (107% yield) of 42.

step 9—To a solution of 42 (333 g, 1.037 mol) in NMP (1.7 L) was added anhydrous powdered potassium ferrocyanide (115 g, 0.312 mol, dried at 100° C. in vacuo, anhydrous $Na_2CO_3$ (110 g, 1.037 mol), Pd(OAc)$_2$ (0.23 g, 0.001 mol) and DPPF (1.15 g, 0.002 mol). The flask was purged with at least 3 vacuum/nitrogen cycles then heated to 130° C. until HPLC indicated the reaction was complete (3 to 6 h). The cooled reaction mixture was filtered through a CELITE® bed, TBME (4 L) was added, and then the mixture washed with water (3×1 L). The organic phase is decolorized with activated charcoal (25 g). After solvent exchange into EtOAc (0.4 L) and hexanes (0.4 L), the mixture was cooled to ca. 0° C. The product was filtered, washed with 20% EtOAc/hexanes (2×0.2 L), and dried in vacuo at 60° C. overnight to afford 223 g (81%) of 44.

step 10—A mixture of 44 (201 g, 752 mmol), toluene (603 mL) and anisole (201 mL) was heated to ca. 50° C. TFA (90.0 g, 790 mmol) was added in one portion and the resulting mixture was heated to ca. 65° C. and aged for about 1 h. The product may crystallize during the reaction which is associated with ca. 10° C. exotherm. The reaction was monitored by HPLC and cooled to RT when complete. The product was filtered, washed sequentially with toluene (2×50 mL) and heptane (1×100 mL), dried in vacuo at 70° C. to afford 106.1 g (95.9%) of 46.

step 11—A solution of 46 (95.0 g, 646 mmol) and THF (665 mL) was cooled to −10° C. and a solution of potassium tert-butoxide in THF (646 mL of a 1M solution, 646 mmol) was added over 15 min. The resulting slurry was maintained at 0° C. for 45 min, cooled to −10° C. and then 37 (182.9 g, 1.03 mol) was added rapidly. The slurry was warmed to 10° C. over 3 h at which point the mixture became homogeneous. The volume was reduced to one third in vacuo and then poured into cold water (2.4 L) with vigorous stirring. After stirring for 30 min, the solid was filtered, washed with water (ca. 150 mL) and partially dried under vacuum at 45° C. The solid was then triturated at 0° C. with enough $Et_2O$ to form a stirrable slurry (ca. 150 mL). The slurry was filtered, washed with cold $Et_2O$ (ca. 150 mL total), and then dried in vacuo at 45° C. to afford 141.4 g (72.0%) of 48.

step 12—To a solution of 48 (140.0 g, 460 mmol) in DCM (1.4 L) was added DEOXO-FLUOR® (203.6 g, 920 mmol) while maintaining the temperature at between 20 and 30° C. After aging overnight the mixture was quenched by dropwise addition of water (380 mL) while cooling with a −15° C. bath. The phases were separated and the organic phase was washed with water (380 mL) followed by saturated $NaHCO_3$ (2×380 mL). The DCM was evaporated under reduced pressure and the residue was taken up in IPA (700 mL) and followed by the addition of 25% sodium bisulfite solution (115 mL). This cloudy mixture was aged for 30 min at 45° C. and then approximately 70% of the IPA was replaced with water by distillation under reduced pressure. After stirring overnight, a mixture of crystals and hardened chunks was isolated by filtration, crushed with a mortar and pestle, and then washed in a filter with water (ca. 250 mL). After partial drying under vacuum at 50° C., the solid was triturated in a minimal amount of cold $Et_2O$ (ca. 80 mL; 0° C.), filtered, and washed with cold $Et_2O$ (ca. 50 mL). The product was dried in vacuo at 50° C. to afford 116.5 g (77.4%) of 38.

EXAMPLE 3

(4-methyl-5-methylsulfanyl-4H-[1,2,4]triazol-3-yl) acetic acid t-butyl ester steps 1 & 2—To a solution of tert-butyl hydrogen malonate (93.7 g, 585 mmol) in MeCN (1.6 L) was added 1,1'-carbonyldiimidazole (93.9 g, 579 mmol) over 20 min at RT. After 1 h 4-methylthiosemicarbazide (92.3 g, 878 mmol) was added over ca. 20 min. After stirring for 1 h, the slurry was heated at reflux for 30 h and then cooled to RT. Concentration in vacuo while replacing with water afforded a slurry. After aging at 0° C., the product was filtered off, washed with water, and dried in vacuo at 50° C. to afford 98.86 g (73.7%) of 24 which was recrystallized from EtOAc.

step 3—A slurry of 24 (125.0 g, 550 mmol) in MeCN (600 mL) was treated with methyl iodide (93.7 g, 660 mmol). After stirring overnight the solution was evaporated to afford a dark brown oil. The residue was dissolved in DCM (250 mL) and washed sequentially with saturated $NaHCO_3$ solution (75 mL), 25% sodium bisulfite solution (75 mL), water (75 mL), and saturated NaCl solution (75 mL). The organic phase was dried (Na$_2$SO$_4$), filtered and evaporated to afford 128.8 g (96.3%) of 4 (R$^1$=Me and R$^3$=tert-Bu) as an oil that solidified on standing at RT.

EXAMPLE 4 steps 1-3—To a solution of 6 (Ar=3-cyano-5-difluoromethyl-phenyl, 18.5 g, 56.7 mmol) and 4 (16.55 g, 68.0 mmol) in THF (93 mL) was slowly added potassium t-butoxide (113.5 mL of a 1M solution in THF, 113.4 mmol) while maintaining the temperature between −20 to −10° C. The mixture was warmed to 0° C., and HOAc (6.5 mL, 113.4 mmol) was added followed by water (110 mL). After warming to RT the organic phase was separated. Most of the THF was evaporated in vacuo, MeCN (65 mL) was added and the solution (ca. 70 mL) was filtered through a CELITE® pad. Methanesulfonic acid (11 mL, 170 mmol) was added and the solution was heated at reflux until the reaction was complete (ca. 4 h). After cooling, the mixture was diluted sequentially with EtOAc (60 mL), water (60 mL) and sufficient saturated K$_2$CO$_3$ to adjust the pH to ca. 7. The aqueous phase was separated, and extracted with EtOAc (20 mL). The combined organic layers were filtered through a CELITE pad and Pd/C catalyst (Johnson Matthey type A503023-5, 3.0 g) and vanadyl acetylacetonate (0.77 g, 2.8 mmol) were added. The mixture was stirred under a hydrogen atmosphere until reduction of the nitro was complete. CELITE (5 g) was added and then the mixture filtered through a CELITE pad (10 g) and the cake washed with MeCN (5×20 mL). The filtrate was washed with a mixture of saturated NaCl (40 mL) and saturated NaHCO$_3$ (40 mL), followed by saturated NaCl (30 mL). The organic phase was concentrated and the product crystallized from EtOAc (40 mL). Hexane (10 ml) was added to the slurry, which was cooled to 0° C. and aged for at least 2 h. The product was filtered off, washed with 17% hexane in EtOAc (3×10 mL) and dried at 55° C. in vacuo to afford 16.86 g (71% yield) of 12.

step 4—A mixture containing 12 (Ar=3-cyano-5-difluoromethyl-phenyl, 41.45 g, 98.8 mmol), Cu(I)Br (57.86 g, 395 mmol), LiBr (26.54 g, 296 mmol) and MeCN (620 mL) in an aluminum foil covered flask was heated to 58° C. After 15 min, tert-butyl nitrite (20.04 mL, 198 mmol) was added over 30 min while maintaining the temperature at ca. 58° C. After the reaction was complete, the mixture was concentrated to a minimum volume (ca. 600 mL solvent was collected). DCM (400 mL) was added followed by 3M HCl (200 mL). The organic phase was separated and washed with 3M HCl (5×100 mL). After neutralization with aqueous K$_2$CO$_3$ to pH ca. 7, the organic layer was washed with 6% sodium thiosulfate solution (690 g), saturated NaHCO$_3$ solution (250 mL), saturated NaCl solution (250 mL), and then filtered through a CELITE pad. p-Toluenesulfonic acid (21 g, 108.7 mmol) was added and solvent was exchanged for EtOH (250 mL) by evaporation under reduced pressure. The volume of the slurry was reduced to ca. 125 mL by evaporation under reduced pressure. The slurry was cooled to RT and aged for at least 2 h. The product was filtered, the solid washed with EtOH (2×50 mL), and dried at 65° C. in vacuo to afford 43.0 g (66.4%) of 14 (2=Br).

step 5—To a mixture of 14 (Ar=3-cyano-5-difluoromethyl-phenyl, R$^2$=Br; 25.0 g, 38 mmol), and HCO$_2$H (4.49 g, 114.4 mmol) in DCM (250 mL) was added 30% H$_2$O$_2$ (25.95 g, 228.8 mmol) over 5 min and the mixture heated at reflux until the reaction was complete. The reaction was quenched with a solution of sodium sulfite (12.5 g, 99.1 mmol) in water (75 mL) and the pH adjusted to ca. 10 with 60% K$_2$CO$_3$ (ca. 25 mL). The aqueous phase was separated and extracted with DCM (2×100 mL). The combined organic extracts were washed with saturated NaCl (200 mL) and filtered through a CELITE pad. The solvent was exchanged for IPA and concentrated to ca. 200 mL. Hexane (50 mL) was added, and after crystals had formed, the mixture was aged at 60° C. for 2 h. The slurry was cooled to 25° C. and aged for 2 h. The product was filtered off, washed with 25% hexane in IPA (3×25 mL) and dried at 65° C. in vacuo to afford 17.7 g (90%) of 18.

step 6—A mixture of 18 (Ar=3-cyano-5-difluoromethyl-phenyl, R$^2$=Br; 9.29 kg, 18.1 mol), Ac$_2$O (3.25 kg, 31.8 mol) and HOAc (36.0 kg) was heated between 105 to 110° C. The mixture was aged for about h and monitored by HPLC. Upon completion, the mixture was cooled to ca. 35 to 45° C. and water (7.5 L) was added. After aging at ca. 45° C. for 8 h, the reaction was analyzed by HPLC. The mixture was cooled to between 15 to 25° C., diluted with water (168 L) and then extracted with EtOAc (102 kg). The organic phase was washed sequentially with water (47 L), 10% NaHCO$_3$ (2×77 L) and water (19 L). The organic phase was concentrated ca. 33 L at atmospheric pressure and the mixture cooled to between 18 to 25° C. Once the crystallization began, heptane (3.9 kg) was slowly added. After cooling to 2° C., the product was filtered off, washed with a mixture of 1:1 EtOAc and heptane and then dried in vacuo at between 50 and 60° C. to afford 6.12 kg (75%) of 20.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A process for preparing a compound of formula 2 wherein Ar is phenyl substituted with 2 or 3 groups independently selected from halogen, cyano and C$_{1-6}$ haloalkyl, R$^f$ is hydrogen, and R$^1$ and R$^3$ are C$_{1-10}$ alkyl, which process comprises the steps of:

(a) contacting 4 with a strong base in an inert solvent to form the conjugate base of 4 and contacting said conjugate base with 6 to afford 8;

(b) exposing 8 to conditions which result in hydrolysis of the ester and decarboxylation of the resulting carboxylic acid to afford 2.

2. A process according to claim 1 wherein Ar is 3-chloro-5-cyano-phenyl, 3,5-dicyano-phenyl or 3-cyano-5-difluoromethyl-phenyl, $R^1$ is methyl and $R^3$ is tert-Bu.

3. A process according to claim 2 wherein said strong base is potassium tert-butoxide, said inert solvent is THF and said hydrolysis conditions comprise methanesulfonic acid in acetonitrile at reflux temperature.

4. A process according to claim 3 wherein Ar is 3-cyano-5-difluoromethyl-phenyl.

5. A process which comprises the steps of claim 1 which process further the steps of:

(a) contacting 2 with a reducing agent capable of selective reduction of the nitro group to afford 12; and, (b) contacting 12 with a diazotizing reagent and either Cu(I)Br/LiBr or Cu(I)Cl/LiCl to afford 14 wherein $R^2$ is bromo and chloro respectively.

6. A process according to claim 5 wherein Ar is 3-cyano-5-difluoromethyl-phenyl, $R^1$ is methyl, $R^2$ is bromide, $R^3$ is tert-butyl, said strong base is potassium tert-butoxide, said inert solvent is THF, said hydrolysis conditions comprise methanesulfonic acid in acetonitrile at reflux temperature said reducing agent is hydrogen, Pd/C and VO(acac)$_2$, said diazotizing reagent is tert-butyl nitrite and said cuprous salt is Cu(I)Br.

7. A process which comprises the steps of claim 6 which process further comprises the step of converting 14 wherein $R^2$ is Br to the tosylate salt.

8. A process according to claim 7 wherein Ar is 3-cyano-5-difluoromethyl-phenyl, $R^1$ is methyl, $R^2$ is bromide, $R^3$ is tert-butyl, said strong base is potassium tert-butoxide, said inert solvent is THF, said hydrolysis conditions comprise methane sulfonic acid in acetonitrile at reflux temperature said reducing agent is hydrogen Pd/C and VO(acac)$_2$, said diazotizing reagent is tert-butyl nitrite, said cuprous salt is Cu(I)Br and said oxidizing agent is MCBPA.

\* \* \* \* \*